United States Patent
Maeda (10) Patent No.: US 8,257,958 B2
(45) Date of Patent: Sep. 4, 2012

(54) MICROORGANISM CAPABLE OF CONTROLLING PLANT DISEASES AND PLANT DISEASE-CONTROLLING AGENT USING THE MICROORGANISM

(75) Inventor: Mitsunori Maeda, Fujieda (JP)

(73) Assignee: Nippon Soda Co., Ltd., Tokyo (JP)

( * ) Notice: Subject to any disclaimer, the term of this patent is extended or adjusted under 35 U.S.C. 154(b) by 350 days.

(21) Appl. No.: 12/312,036

(22) PCT Filed: Nov. 6, 2007

(86) PCT No.: PCT/JP2007/071531
§ 371 (c)(1),
(2), (4) Date: May 5, 2009

(87) PCT Pub. No.: WO2008/056653
PCT Pub. Date: May 15, 2008

(65) Prior Publication Data
US 2009/0324564 A1 Dec. 31, 2009

(30) Foreign Application Priority Data

Nov. 8, 2006 (JP) ................................ 2006-302263

(51) Int. Cl.
*C12N 1/20* (2006.01)
(52) U.S. Cl. .................................. 435/253.3; 424/93.47
(58) Field of Classification Search ........................ None
See application file for complete search history.

(56) References Cited

FOREIGN PATENT DOCUMENTS

| JP | A-2001-247423 | 9/2001 |
| JP | A-2001-302407 | 10/2001 |
| JP | A-2005-325077 | 11/2005 |
| WO | WO 95/20040 A1 | 7/1995 |
| WO | WO 01/03507 A1 | 1/2001 |
| WO | WO 02/072795 A2 | 9/2002 |
| WO | WO 2004/024865 A2 | 3/2004 |

OTHER PUBLICATIONS

Sessitsch et al., Can. J. Microbiol. 50: 239-249 (2004).*
Validov et al., Journal of Applied Microbiology 102 (2007) 461-471(,Article first published online: Aug. 1, 2006).*
Meyer et al., Applied and Environmental Microbiology, Jun. 2002, p. 2745-2753.*
Kloepper et al., Current Microbiology vol. 4 (1980), pp. 317-320.*
Coroler et al.; "*Pseudomonas rhodesiae* sp. nov., a New Species Isolated from Natural Mineral Waters;" *System. Appl. Microbial.*; 1996; pp. 600-607; vol. 19.
Kahng et al; "PAH utilization by *Pseudomonas rhodesiae* KK1 isolated from a former manufactured-gas plant site;" *Appl. Microbiol. Biotechnol*; 2002; pp. 475-480; vol. 60.
Fontanille et al.; "Optimization of isonovalal production from α-pinene oxide using permeabilized cells of *Pseudomonas rhodesiae* CIP 107491;" *Appl. Microbiol Biotechnol*; 2003; pp. 534-540; vol. 60.
Fontanille et al., "Optimization of isonovalal production from α-pinene oxide using permeabilized cells of *Pseudomonas rhodesiae* CIP 107491," *Appl Microbiol Biotechnol*, Dec. 4, 2002, pp. 534-540, vol. 60.
Validov , Shamil, "Biocontrol of tomato foot and root rot by *Pseudomonas* bacteria in stonewool," Thesis, 2007, openaccess. leidenuniv.nl, ISBN: 978-90-9022475-6, 1-192.
Supplementary European Search Report dated Jun. 15, 2011, in corresponding European Application No. EP 07831263.4, 6 pages.
Kang et al., "Two Bacterial Entophytes Eliciting Both Plant Growth Promotion and Plant Defense on Pepper (*Capsicum annuum* L.)," J. Microbiol. Biotechnol., Jan. 2007, 17(1):96-103.
Keel et al,. "*Pseudomonads* as Antagonists of Plant Pathogens in the Rhozosphere: Role of the Antibiotic 2,4-Diacetyiphioroglucinol in the Suppression of Black Root Rot of Tobacco," Symbiosis, Jan. 1, 1990, 9:327-341.
Weller, David M., "*Pseudomonas* Biocontrol Agents of Soilborne Pathogens: Looking Back Over 30 Years," Phytopathology, Feb. 2007, 97(2):250-256.

* cited by examiner

*Primary Examiner* — Irene Marx
(74) *Attorney, Agent, or Firm* — Foley & Lardner LLP (57) ABSTRACT

The object of the present invention is to provide a microorganism which places little burden on the environment, shows an extremely low possibility of a resistant pathogenic bacterium to emerge, and has a superior controlling ability against various plant diseases (in particular, soft rot and canker of leaf and root vegetables); a plant disease controlling agent containing the microorganism; and a method for controlling plant diseases comprising applying the plant disease controlling agent to the plant and/or the grove soil thereof. A plant disease controlling agent is used which contains a bacterial cell of *Pseudomonas rhodesiae* having controlling ability against plant diseases, preferably a bacterial cell of *Pseudomonas rhodesiae* FERM BP-10912 or its variant having controlling ability against plant diseases.

4 Claims, 1 Drawing Sheet

SEQUENCE LISTING

<160> NUMBER OF SEQ ID NOS: 3

<210> SEQ ID NO 1
<211> LENGTH: 1422
<212> TYPE: DNA
<213> ORGANISM: Pseudomonas rhodesiae

<400> SEQUENCE: 1

```
ggcctaacac atgcaagtcg agcggtagag agaagcttgc ttctcttgag agcggcggac     60
gggtgagtaa tgcctaggaa tctgcctggt agtgggggat aacgttcgga aacgacgct    120
aataccgcat acgtcctacg ggagaaagca ggggaccttc gggccttgcg ctatcagatg    180
agcctaggtc ggattagcta gttggtgggg taatggctca ccaaggcgac gatccgtaac    240
tggtctgaga ggatgatcag tcacactgga actgagacac ggtccagact cctacgggag    300
gcagcagtgg ggaatattgg acaatgggcg aaagcctgat ccagccatgc cgcgtgtgtg    360
aagaaggtct tcggattgta aagcacttta agttgggagg aagggccatt acctaatacg    420
tgatggtttt gacgttaccg acagaataag caccggctaa ctctgtgcca gcagccgcgg    480
taatacagag ggtgcaagcg ttaatcggaa ttactgggcg taaagcgcgc gtaggtggtt    540
tgttaagttg gatgtgaaat ccccgggctc aacctgggaa ctgcattcaa aactgactga    600
ctagagtatg gtagagggtg gtggaatttc ctgtgtagcg gtgaaatgcg tagatatagg    660
aaggaacacc agtggcgaag gcgaccacct ggactgatac tgacactgag gtgcgaaagc    720
gtggggagca acaggatta gataccctgg tagtccacgc cgtaaacgat gtcaactagc    780
cgttgggagc cttgagctct tagtggcgca gctaacgcat taagttgacc gcctggggag    840
tacggccgca aggttaaaac tcaaatgaat tgacgggggc ccgcacaagc ggtggagcat    900
gtggtttaat tcgaagcaac gcgaagaacc ttaccaggcc ttgacatcca atgaactttc    960
tagagataga ttggtgcctt cgggaacatt gagacaggtg ctgcatggct gtcgtcagct   1020
cgtgtcgtga gatgttgggt taagtcccgt aacgagcgca accttgtcc ttagttacca   1080
gcacgttatg gtgggcactc taaggagact gccggtgaca aaccggagga aggtggggat   1140
gacgtcaagt catcatggcc cttacggcct gggctacaca cgtgctacaa tggtcggtac   1200
aaaggggttgc caagccgcga ggtggagcta atcccataaa accgatcgta gtccggatcg   1260
cagtctgcaa ctcgactgcg tgaagtcgga atcgctagta atcgcgaatc agaatgtcgc   1320
ggtgaatacg ttcccgggcc ttgtacacac cgcccgtcac accatgggag tgggttgcac   1380
cagaagtagc tagtctaacc ttcgggggga cggttaccac gg                      1422
```

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct 16S 27F primer

<400> SEQUENCE: 2

```
agagtttgat cctggctcag                                                 20
```

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct 16S 1544R primer -continued

```
<400> SEQUENCE: 3
agaaaggagg tgatccagcc                                                    20
```

MICROORGANISM CAPABLE OF CONTROLLING PLANT DISEASES AND PLANT DISEASE-CONTROLLING AGENT USING THE MICROORGANISM

TECHNICAL FIELD

The present invention relates to a microorganism having controlling ability against plant diseases, a plant disease controlling agent comprising a bacterial cell of the microorganism, and a method for controlling plant diseases using the microorganism.

BACKGROUND ART

The present application claims priority based on Japanese Application No. 2006-302263 filed on Nov. 8, 2006.

Conventionally, inorganic or organic copper agents, and antibiotics such as kasugamycin, streptomycin and oxytetracycline are used against bacterial diseases in various agricultural and horticultural crops. In addition, oxolinic acid was registered in 1989 as a synthetic antibacterial agent and has largely contributed to the increase of crop production. However, inorganic and organic copper agents tend to cause crop injury to agricultural and horticultural crops, so that timing and target crops are restricted in using the inorganic and organic agents. Further, antibiotics have drawbacks in that as a result of continuously using an antibiotic, the bacterial pathogen gains resistance to the antibiotic. With respect to oxolinic acid as well, the resistant bacteria has emerged recently and its use is restricted.

Therefore, in order to overcome the problems of crop injuries and resistant bacteria, there has been an increased interest in biological pesticides as a means for substituting for conventional synthetic fungicides or as a means for using in combination with the conventional synthetic fungicides. Biological pesticides are advantageous in that they cause very little environmental pollution, harmonize with ecosystem, and are superior in the controlling effect as compared to conventional synthetic fungicides. Those known as a microbial agrochemical used for controlling bacterial disease in agricultural and horticultural crops include, for example, non-pathogenic *Erwinia carotovora* particularly used for controlling bacterial soft rot of leaf and root vegetables; and *Pseudomonas* sp. CAB-02 or *Trichoderma atroviride* particularly used for controlling bacterial grain rot and bacterial seedling blight, that are contagious bacterial diseases in rice seeds. Bactericidal compositions for agriculture and horticulture containing such microorganism have been developed and marketed. Further, Patent document 1 describes *Pseudomonas fluorescens* strain G7090 having controlling effect against *Pseudomonas cichorii* which is a causal bacterium of bacterial rot of lettuce.

Microbial agrochemicals, however, generally target only restricted number of plant diseases and often do not exert satisfactory effect against other plant diseases. For example, non-pathogenic *Erwinia carotovora* only targets bacterial soft rot of leaf and root vegetables, *Pseudomonas* sp. CAB-02 or *Trichoderma atroviride* only targets rice diseases, and *Pseudomonas fluorescens* only targets bacterial rot of lettuce. As such, target diseases are restricted and almost no effect can be expected for other bacterial diseases. Further, because pathogenic *Erwinia carotovora* is controlled by bacteriocin which is an antibacterial protein produced by non-pathogenic *Erwinia carotovora*, it is concerned that non-pathogenic *Erwinia* carotovora may acquire resistance to bacteriocin (e.g., non-patent reference 1).

Patent Reference 1: Japanese Laid-Open Patent Application No.
Non-patent Reference 1: Biological control of crop diseases by antagonistic microorganisms, III-5, Control of vegetable bacterial soft rot by non-pathogenic *Erwinia carotovora*, Kumiai Chemical Industry Co. Ltd., 65-76: 2003

DISCLOSURE OF THE INVENTION

Object to be Solved by the Invention

The present invention was made in view of the situation mentioned above. The object of the present invention is, therefore, to provide a microorganism which has a superior controlling ability against various plant diseases (in particular, bacterial soft rot or bacterial rot of leaf and root vegetables, canker of citrus, and bacterial shot hole of peaches) while having less burden on the environment and an extremely low possibility of a resistant pathogenic bacterium to emerge; a plant disease controlling agent comprising a bacterial cell of the microorganism; and a method for controlling plant diseases comprising applying the plant disease controlling agent to a plant and/or grove soil thereof.

Means to Solve the Object

In order to solve the object, the present inventors focused on resident microorganisms of lettuce and searched for microorganisms having controlling ability against plant diseases. As a result, the present inventors found a microorganism having superior controlling effect against bacterial soft rot of lettuce. Mycological properties and the base sequence of the 16SrDNA gene of the microorganism were analyzed and the microorganism was presumed to be a novel strain of *Pseudomonas rhodesiae*. The present invention was made based on the finding as above.

The present invention relates to (1) *Pseudomonas* rhodesiae having controlling ability against a plant disease; (2) *Pseudomonas rhodesiae* FERM BP-10912 having controlling ability against a plant disease; (3) a variant of *Pseudomonas* rhodesiae FERM BP-10912, wherein the variant has controlling ability against a plant disease; (4) *Pseudomonas rhodesiae*, *Pseudomonas rhodesiae* FERM BP-10912, or a variant of *Pseudomonas rhodesiae* FERM BP-10912 according to any one of (1) to (3), wherein the plant disease is one or more diseases selected from canker, bacterial shot hole, bacterial soft rot, bacterial spot, bacterial black spot, bacterial wilt, necrotic leaf spot, pitch necrosis, bacterial grain rot, bacterial seedling blight, bacterial leaf blight, bacterial rot, and black rot; and (5) *Pseudomonas rhodesiae*, *Pseudomonas rhodesiae* FERM BP-10912, or a variant of *Pseudomonas rhodesiae* FERM BP-10912 according to any one of (1) to (3), wherein the plant disease is a disease in a plant caused by one or more pathogenic bacteria selected from *Xanthomonas* genus, *Erwinia* genus, *Pseudomonas* genus, *Ralstonia* genus, and *Burkholderia* genus according to any one of (1) to (3).

The present invention further relates to (6) a plant disease controlling agent containing a bacterial cell of *Pseudomonas rhodesiae* having controlling ability against a plant disease; (7) the plant disease controlling agent according to (6), wherein the bacterial cell of *Pseudomonas* rhodesiae is one or more bacterial cells selected from the group consisting of a bacterial cell of *Pseudomonas rhodesiae* FERM BP-10912 according to (2), and a bacterial cell of a variant of *Pseudomonas rhodesiae* FERM BP-10912 according to (3); and (8) the plant disease controlling agent according to (6), wherein the plant disease is one or more plant diseases selected from canker, bacterial shot hole, bacterial soft rot, bacterial spot, bacterial black spot, bacterial wilt, necrotic leaf spot, pitch necrosis, bacterial grain rot, bacterial seedling blight, bacterial leaf blight, bacterial rot, and black rot.

The present invention still further relates to (9) a method for controlling a plant disease, wherein *Pseudomonas rhodesiae*, *Pseudomonas rhodesiae* FERM BP-10912, or a variant of *Pseudomonas rhodesiae* FERM BP-10912 according to any one of (1) to (3) is applied to a plant and/or grove soil of the plant.

Effect of the Invention

A plant disease controlling agent and a method for controlling plant diseases of the present invention place little burden on the environment and show an extremely low possibility of resistant pathogenic bacteria to emerge, as well as retaining a superior controlling ability against various plant diseases for a longer period. Further, a plant disease controlling agent of the present invention are remarkably advantageous compared to conventional microbial agrochemicals in that it exerts a superior effect particularly against bacterial soft rot, bacterial rot or black rot of leaf and root vegetables, canker of citrus, and bacterial shot hole of peaches among plant diseases.

BEST MODE OF CARRYING OUT THE INVENTION

Microorganisms of the Present Invention

A microorganism of the present invention is not particularly limited as long as it is *Pseudomonas rhodesiae* having controlling ability against a plant disease. "Having controlling ability against a plant disease" herein means having an antagonistic action against the pathogenic bacterium of any of plant diseases. A microorganism of the present invention prevents or cures a plant disease caused by the pathogenic bacterium of the plant disease by exerting an antagonistic action against said pathogenic bacterium. A microorganism of the present invention, however, is particularly effective in preventing a plant disease.

"Prevents a plant disease" herein refers to that when a plant or grove soil thereof which has not been infected with a pathogenic bacterium of a plant disease or has not displayed any symptom thereof is grown either under the preferred conditions plus treatment with a microorganism of the present invention or only under the preferred conditions, the plant treated with a microorganism of the present invention shows a lower degree of disease compared to the plant untreated with a microorganism of the present invention. Further, "cures a plant disease" as mentioned above refers to that when a plant which has been infected with the pathogenic bacterium of a plant disease and shows the symptom thereof is grown under the preferred conditions except that the plant is treated or untreated with a microorganism of the present invention, a plant treated with a microorganism of the present invention shows a lower degree of disease compared to a plant untreated with a microorganism of the present invention.

"Shows a lower degree of disease" means, for example, that the disease severity (or onset rate) is low and the preventive value is greater than 0. The higher the preventive value is, the more it is preferred. Hence, the preventive value of 30 or more is superior, 50 or more is more superior, and 60 or 70 or more is particularly superior.

A microorganism of the present invention is preferably exemplified by *Pseudomonas rhodesiae* 05057219 strain, *Pseudomonas rhodesiae* JCM11940 strain, and variants of these, among which *Pseudomonas rhodesiae* 05057219 strain and its variants are more preferably exemplified because of their better properties as a plant disease controlling agent. *Pseudomonas rhodesiae* 05057219 strain was domestically deposited by the applicant of the present application on Sep. 12, 2006 at International Patent Organism Depositary (IPOD), National Institute of Advanced Industrial Science and Technology (AIST) (Tsukuba Central 6, 1-1-1 Higashi, Tsukuba, Ibaraki, Japan) under the accession number FERM P-21025, followed by international deposit on Sep. 25, 2007 under the international accession number FERM BP-10912. *Pseudomonas rhodesiae* JCM11940 strain was deposited at RIKEN, Ibaraki Institute, BioResource Center (3-1-1 Koyadai, Tsukuba-shi, Ibaraki, Japan) as JCM11940.

"A variant of a certain strain X" in the present specification encompasses any variant induced from the strain X, as long as such variant has the same mycological properties as those of a certain strain X and having controlling ability against plant diseases. Variation includes an artificial variation caused by such as a chemical variant agent or ultraviolet, as well as a naturally occurring variation. A variant of a certain strain X is preferably exemplified by those variants having the same mycological properties as those of a certain strain X in respect of the properties described in Table 1 below, and having controlling ability against plant diseases.

*Pseudomonas rhodesiae* 05057219 strain (FERM BP-10912) which is preferred among the microorganisms of the present invention has following mycological properties.

*Pseudomonas rhodesiae* 05057219 strain is a Gram-negative, rod-shaped bacterium, which does not form spore. Its full cell length is 2.0-2.5 μm, the full width is 0.7-0.8 μm, and motility is observed. It forms a smooth circular colony on a broth agar medium and produces fluorescent pigment on a King B medium. Its growth is not observed at 41° C. It is positive for catalase activity, oxidized in the OF test, negative for nitrate salt reduction, negative for indole production, negative for urease activity, positive for gelatin degradation, negative for β-galactosidase activity, and negative for β-glucosidase activity. Further, in LOPAT test, it is positive for levan production, negative for potato tuber rot, negative for tobacco hypersensitive response, positive for oxidase activity, and positive for arginine degradation. It is negative for starch assimilation. As to assimilation of carbon compounds such as sugar and organic acids, it is positive for D-glucose, positive for L-arabinose, positive for D-mannose, positive for D-mannitol, positive for N-acetyl-D-glucosamine, negative for maltose, positive for potassium gluconate, positive for n-capric acid, negative for adipic acid, positive for dL-malic acid, positive for sodium citrate, negative for phenyl acetate, positive for sucrose, positive for trehalose, negative for adonit, positive for sorbitol, positive for butyric acid, positive for propionic acid, and positive for propylene glycol. The determination method and the like for each item are as described later in the Examples.

A microorganism of the present invention will suffice if it has controlling ability against at least one plant disease, but it is preferred that it has controlling ability against at least 1 or more, preferably 2 or more, and more preferably against all of the plant diseases selected from canker, bacterial shot hole, bacterial soft rot, bacterial spot, bacterial black spot, bacterial wilt, necrotic leaf spot, pitch necrosis, bacterial grain rot, bacterial seedling blight, bacterial leaf blight, bacterial rot, and black rot. Further, it is preferred that a microorganism of the present invention especially has controlling ability against 1 or more, preferably 2 or more, and more preferably all of the plant diseases from among bacterial soft rot, bacterial rot, black rot, canker and bacterial shot hole.

Examples of the pathogenic bacterium of these plant diseases include such as 1 or more pathogenic bacteria belonging to *Xanthomonas* genus, *Erwinia* genus, *Pseudomonas* genus, *Ralstonia* genus, and *Burkholderia* genus. While further details are shown in Table 1, the pathologic bacteria related to the present invention are not restricted to these.

bacterial cell of *Pseudomonas rhodesiae* of the present invention contained in the controlling agent exerts an antagonistic action against the pathogenic bacterium. A plant disease controlling agent of the present invention may be used as a plant disease preventive agent or a plant disease therapeutic agent, where it is especially effective as a plant disease preventive agent.

*Pseudomonas rhodesiae* mainly takes a form of trophocyte, but the bacterial cell of *Pseudomonas rhodesiae* of the present invention may take any cell form (e.g., dormant cell) that viable bacteria of *Pseudomonas rhodesiae* may take such as trophocyte of *Pseudomonas rhodesiae*. Further, a form of the bacterial cell of *Pseudomonas rhodesiae* to be used for a

TABLE 1

| Plant disease | Pathogenic bacterium | Examples of target plants |
|---|---|---|
| Canker | *Xanthomonas campestris* pv. *citri* | Citrus |
| Bacterial shot hole | *Xanthomonas campestris* pv. *pruni* | Peach, etc. |
| Bacterial soft rot | *Erwinia carotovora* subsp. *carotovora* | Leaf vegetables such as lettuce and Chinese cabbage; root vegetables such as Japanese radish and potatoes; flowers such as sunflower, orchid and cyclamen |
| Bacterial spot | *Pseudomonas marginalis* pv. *marginalis* | Cucumber, etc. |
| | *Xanthomonas campestris* pv. *raphani* | Japanese radish |
| | *Pseudomonas syringae* pv. *lachrymans* | Melon |
| Bacterial leaf spot | *Pseudomonas syringae* pv. *maculicola* | Japanese radish, Chinese cabbage |
| Bacterial black spot | *Pseudomonas viridiflava* | Tomato |
| Bacterial wilt | *Ralstonia solanacearum* | Tomato, eggplant, pepper, etc. |
| Necrotic leaf spot | *Xanthomonas campestris* pv. *cucurbitae* | Cucumber, etc. |
| Pith necrosis | *Pseudomonas corrugata*, *Pseudomonas fluorescens* | Tomato, eggplant, etc. |
| Bacterial grain rot | *Burkholderia glumae* | Rice |
| Bacterial seedling blight | *Burkholderia plantarii* | Rice |
| Bacterial leaf blight | *Xanthomonas oryzae* pv. *oyzaer* | Rice |
| Bacterial spot | *Pseudomonas cichorii* *Pseudomonas marginalis* pv. *marginalis* | Lettuce, Chinese cabbage, cabbage, etc. |
| Black rot | *Xanthomonas campestris* pv. *campestris* | Cabbage, etc. |

An applicable plant for a microorganism of the present invention is not particularly limited as long as the microorganism of the present invention can exert controlling ability to that plant. Examples of the applicable plant include a plant belonging to Brassicaceae, Solanaceae, Cucurbitaceae, Liliaceae, Fabaceae, Compositae, Chenopodiaceae, Poaceae, Rosaceae, Caryophyllaceae, Primulaceae, Rutaceae, Vitaceae, Actinidiaceae, Ebenaceae, Actinidiaceae, Convolvulaceae, or Araceae. Preferably exemplified among these are a plant belonging to Brassicaceae such as Chinese cabbage, a plant belonging to Compositae such as lettuce, a plant belonging to Solanaceae such as potato, a plant belonging to Rutaceae such as lemon and navel, and a plant belonging to Rosaceae such as peach.

<2> Plant Disease Controlling Agents of the Present Invention

A plant disease controlling agent of the present invention is not particularly limited as long as it contains the bacterial cell of *Pseudomonas rhodesiae* of the present invention. A strain of *Pseudomonas rhodesiae* of the present invention to be contained in a plant disease controlling agent of the present invention may be either 1 type or 2 or more types.

A plant disease controlling agent of the present invention prevents or cures a plant disease caused by a pathogenic bacterium of a plant disease through the process that the plant disease controlling agent of the present invention may be either 1 type or more than 2 types.

The bacterial cell of *Pseudomonas rhodesiae* used for a plant disease controlling agent of the present invention is obtained, for example, by culturing *Pseudomonas rhodesiae* of the present invention which has been isolated and obtained by using as an index the 16SrDNA gene sequence of *Pseudomonas* rhodesiae 050572I9 strain (FERM BP-10912) (see SEQ ID No. 1) and/or the above-mentioned mycological properties of the strain. A method for culturing *Pseudomonas rhodesiae* of the present invention is not particularly limited, regardless of the media type or culture conditions, as long as it is a method wherein the bacterial cell of *Pseudomonas rhodesiae* can proliferate. When employing a solid culture, a method is exemplified wherein stationary culture is carried out at 20-35° C. by using a Standard method agar, Nutrient agar, potato dextorose agar medium, etc., and when employing a liquid culture, a method is exemplified wherein shaking/stirring culture is carried out at 20-35° C. by using various liquid media, etc. in which agar has been removed from the above-mentioned agar media.

As for the bacterial cell of *Pseudomonas rhodesiae*, any cell form such as the bacterial cell per se of *Pseudomonas rhodesiae*, a suspension containing the bacterial cell, a culture solution containing the bacterial cell, and a concentrate, paste, dried substance or dilution of these (hereinafter may be referred to as "bacterial cell and the like of *Pseudomonas rhodesiae*") may be used for a plant disease controlling agent of the present invention.

The concentration of a bacterial cell of *Pseudomonas rhodesiae* contained in a plant disease controlling agent of the present invention is not particularly limited as long as the effect of the present invention is not affected. When a plant disease controlling agent is diluted to 1,000-2,000 folds, preferably exemplified is a concentration in a range of $1 \times 10^2$-$1 \times 10^{11}$ cfu/ml, preferably $1 \times 10^4$-$1 \times 10^9$ cfu/ml, in terms of bacterial cell concentration.

A plant disease controlling agent of the present invention may contain optional components other than the bacterial cell of *Pseudomonas rhodesiae* of the present invention, as long as the effect of the present invention is not affected. There is no particular limitation for the optional component as long as the effect of the present invention is not affected and examples include a carrier, surfactant, dispersant and supplement. Further, an antioxidant, colorant, lubricant, ultraviolet absorber, antistatic and antiseptic may be added according to need.

Examples of the carrier include inorganic salts such as calcium carbonate; potassium chloride, sodium sulfate, calcium sulfate, ammonium sulfate; organic acids such as citric acid, malic acid and stearic acid, and salts thereof; sugars such as glucose, lactose and sucrose; and a solid carrier such as alumina powder, silica-gel, zeolite, hydroxyapatite, zirconium phosphate, titanium phosphate, titanium oxide, zinc oxide, hydrotalcite, kaolinite, montmorillonite, talc, clay, diatomite, bentonite, white carbon, kaolin and vermiculite.

Further, the surfactant (also can be used as a dispersant) is not particularly limited as long as it can be used for an ordinary agricultural and horticultural formulations, and the specific examples include a nonionic surfactant, anionic surfactant, cationic surfactant and ampholytic surfactant, as described below.

Examples of the nonionic surfactant include a sugar ester surfactant such as sorbitan fatty acid ester($C_{12-18}$), POE sorbitan fatty acid ester($C_{12-18}$), and sucrose fatty acid ester; a fatty acid ester surfactant such as POE fatty acid ester($C_{12-18}$), POE resin acid ester, POE fatty acid diester($C_{12-18}$); an alcohol surfactant such as POE alkylether($C_{12-18}$); an alkylphenol surfactant such as POE alkyl($C_{8-12}$)phenylether, POE dialkyl ($C_{8-12}$)phenylether, and POE alkyl($C_{8-12}$)phenylether formalin condensate; polyoxyethylene polyoxypropylene blockpolymer; a polyoxyethylene-polyoxypropylene blockpolymer surfactant such as alkyl($C_{12-18}$) polyoxyethylene-polyoxypropylene blockpolymer ether; an alkylamine surfactant such as POE alkylamine($C_{12-18}$) and POE fatty acid amide($C_{12-18}$); a bisphenol surfactant such as POE fatty acid bisphenylether; a multi aromatic ring surfactant such as POA benzylphenyl (or phenylphenyl)ether and POA styrylphenyl (or phenylphenyl)ether; a silicon or fluorine surfactant such as POE ether and POE ester silicon surfactants and fluorine surfactant; a plant oil surfactant such as POE castor oil and POE hardened castor oil.

Examples of the anionic surfactant include a sulfate surfactant such as alkylsulfate ($C_{12-18}$, Na, NH$_4$, alkanolamine), POE alkylethersulfate ($C_{12-18}$, Na, NH$_4$, alkanolamine), POE alkylphenylethersulfate ($C_{12-18}$, NH$_4$, alkanolamine), POE benzyl (or styryl) phenyl (or phenylphenyl)ethersulfate (Na, NH$_4$, alkanolamine), polyoxyethylene, polyoxypropylene blockpolymer sulfate (Na, NH$_4$, alkanolamine); a sulfonate surfactant such as paraffin(alkane)sulfonate($C_{12-22}$, Na, Ca, alkanolamine), AOS($C_{14-16}$, Na, alkanolamine), dialkyl sulfosuccinate($C_{8-12}$, Na, Ca, Mg), alkylbenzene sulfonate(Cl$_2$, Na, Ca, Mg, NH$_4$, alkylamine, alkanol, amine, cyclohexylamine), mono- or di-alkyl($C_{3-6}$)naphthalene sulfonate(Na, NH$_4$, alkanolamine, Ca, Mg), naphthalene sulfonate-formalin condensate(Na, NH$_4$), alkyl($C_{8-12}$)diphenylether disulfonate(Na, NH$_4$), ligninsulfonate(Na, Ca), POE alkyl($C_{8-12}$) phenylether sulfonate(Na), and POE alkyl($C_{12-18}$)ether sulfosuccinic acid half ester(Na); a phosphate surfactant such as POE alkyl($C_{12-18}$)etherphosphate(Na, alkanolamine) including a carboxylic acid fatty acid salt($C_{12-18}$, Na, K, NH$_4$, alkanolamine), N-methyl-fatty acid sarcosinate($C_{12-18}$, Na) and resin acid salt (Na, K), POE mono- or di-alkyl($C_{8-12}$) phenyletherphosphate(Na, alkanolamine), POE benzylated (or styrylated)phenyl(or phenylphenyl)etherphosphate(Na, alkanolamine), polyoxyethylene-polyoxypropylene blockpolymer(Na, alkanolamine), phosphatidylcholine phosphatidylethanolimine(lecitin), and alkyl($C_{8-12}$) phosphate.

Examples of the cationic surfactant include an ammonium surfactant such as alkyltrimethylammonium chloride ($C_{12-18}$), methyl-polyoxyethylene-alkylammonium chloride ($C_{12-18}$), alkyl-N-methylpyridium bromide($C_{12-18}$), mono- or di-alkyl($C_{12-18}$)methylated ammonium chloride, and alkyl ($C_{12-18}$)pentamethylpropylenediamine dichloride; and a benzalkonium surfactant such as alkyldimethylbenzalkonium chloride($C_{12-18}$), and benzethonium chloride(octylphenoxyethoxy ethyldimethylbenzylammonium chloride).

Examples of the ampholytic surfactant include a betaine surfactant such as dialkyl($C_{8-12}$)diaminoethylbetaine and alkyl($C_{12-18}$)dimethylbenzylbetaine; a glycine surfactant such as dialkyl($C_{8-12}$)diaminoethylglycine and alkyl($C_{12-18}$) dimethylbenzylglycine.

A surfactant and/or a dispersant may be used alone or in combination of 2 or more kinds thereof.

The supplement can be exemplified by carboxymethylcellulose, polyethyleneglycol, gum Arabic, and starch.

Form of a plant disease controlling agent of the present invention is not particularly limited and it can take any form that a common agricultural and horticultural agent may take. The control agent may take, for example, powder formulation, wettable powder, emulsion, flowable formulation, and granular formulation.

A plant disease to which a plant control agent of the present invention can be applied is not particularly limited as long as the disease is caused when a plant is infected with a pathogenic bacterium to which *Pseudomonas rhodesiae* of the present invention exerts its controlling ability. Examples of the applicable plant disease include canker, bacterial shot hole, bacterial soft rot, bacterial spot, bacterial black spot, bacterial wilt, necrotic leaf spot, pitch necrosis, bacterial grain rot, bacterial seedling blight, bacterial leaf blight, bacterial rot, and black rot.

Further, examples of the plant disease to which a plant control agent of the present invention can be applied include one or more plant diseases, preferably 2 or more plant disease, and more preferably all of the plant diseases selected from canker, bacterial shot hole, bacterial soft rot, bacterial spot, bacterial black spot, bacterial wilt, necrotic leaf spot, pitch necrosis, bacterial grain rot, bacterial seedling blight, bacterial leaf blight, bacterial rot, and black rot. Particularly exemplified are at least 1 or more plant diseases, preferably 2 or more plant diseases, and more preferably all of the plant diseases selected from bacterial soft rot, bacterial rot, black rot, canker and bacterial shot hole.

<3> Method for Controlling Plant Diseases According to the Present Invention

A method for controlling plant diseases according to the present invention is not particularly limited as long as it is a method comprising treating a plant and/or grove soil thereof with a plant disease controlling agent of the present invention, and it can be appropriately selected depending on such as a type of the plant disease and a type of the applicable plant in a similar manner to when ordinary chemical pesticides are used. For example, a plant may be treated with a plant disease controlling agent of the present invention by being, for instance, directly applied or sprayed with a plant disease controlling agent of the present invention. Alternatively, the soil where the plant is grown (grove soil of the plant) may be treated with a plant disease controlling agent of the present invention by being, for instance, mixed, sprayed or irrigated with a plant disease controlling agent of the present invention. Herein, when a plant disease controlling agent of the present invention is treated on the grove soil of a plant, either the plant may be planted after the soil has been treated with a plant disease controlling agent of the present invention, or the soil may be treated with a plant disease controlling agent of the present invention after the plant has been planted to the soil. Further, as described in Japanese Laid-open Patent Application No. 2001-302407, a plant disease controlling agent of the present invention may be placed at the vicinity of blasting opening of a blower for blowing air in the facility and the agrochemical is scattered along with air blown from the blasting opening.

When treating a plant and/or the grove soil thereof with a plant disease controlling agent of the present invention, the plant disease controlling agent of the present invention may be used by diluting it with an appropriate amount of water and the like. The amount of a plant disease controlling agent of the present invention to be treated to a plant and/or the grove soil thereof cannot be generally defined, since the amount differs depending on a type of the plant disease, a type of the applicable plant, etc. When the control agent is sprayed on the soil, the amount may be usually defined to be in a range of $1 \times 10^2$-$1 \times 10^{11}$ cfu/ml, preferably $1 \times 10^4$-$1 \times 10^9$ cfu/ml, in terms of the bacterial cell concentration of *Pseudomonas rhodesiae*.

Number of spray treatments may be appropriately selected according to a type of the plant disease, a type of the applicable plant, and the degree of the disease.

The present invention is explained in more detail in the following, yet the technical scope of the present invention shall not be limited to these exemplifications.

EXAMPLES

Example 1

Identification of the Bacteria and Preparation of a Plant Disease Controlling Wettable Powder Composition 1. Selection of a Strain Having Controlling Ability Against Bacterial Soft Rot of Lettuce Lettuce leaves collected in the farm field were homogenized in a small amount of sterilized water. The suspension thus obtained was coated onto a Standard method agar (0.5% (w/v) Casein Peptone, 0.25% (x/v) yeast extract, 0.1% (w/v) glucose, 1.5% (w/v) agar, pH 6.9-7.1 after the sterilization) (NISSUI PHARMACEUTICAL CO. LTD.) and cultured for 2 days at 25° C. Colonies of the grown microorganisms were collected, which were further separated and obtained as a single colony. Plural strains of the microorganisms thus obtained underwent a test for assessing controlling effect against bacterial soft rot of lettuce (indoor test) as described in the following Examples, for selecting strains of microorganisms having controlling effect against a pathogenic strain of lettuce bacterial soft rot (*Erwinia carotovora*). The strains thus selected further underwent a test for assessing controlling effect against bacterial soft rot of lettuce (field test) in a similar manner to the later-mentioned test for assessing controlling effect against bacterial soft rot in Chinese cabbage (field test). As a result, 0505720 strain was selected which exerted controlling effect against bacterial soft rot of lettuce in the field test as well.

2. Analysis of the 16SrDNA Gene

In order to analyze the nucleotide sequence of the 16SrDNA gene in 05057219 strain, it was attempted to isolate 16SrDNA from 05057219 strain. Specifically, the genomic DNA was isolated from 05057219 strain according to a common protocol. By using thus obtained genomic DNA as a template, PCR amplification was carried out by using 27F primer (SEQ ID No: 2) and 1544R primer (SEQ ID No: 3) that are commonly used primers to isolate 16SrDNA. After presence or absence of the PCR products were confirmed by electrophoresis using agarose gel, each of the PCR products including plural types of polynucleotides were sequenced, and plural types of nucleotide sequences were determined. Assembly was carried out based on the information of thus obtained plural types of nucleotide sequences to determine the full length nucleotide sequence of 16SrDNA. The nucleotide sequence of 16SrDNA gene of 05057219 strain is shown below as SEQ ID No: 1.

Figure 1:
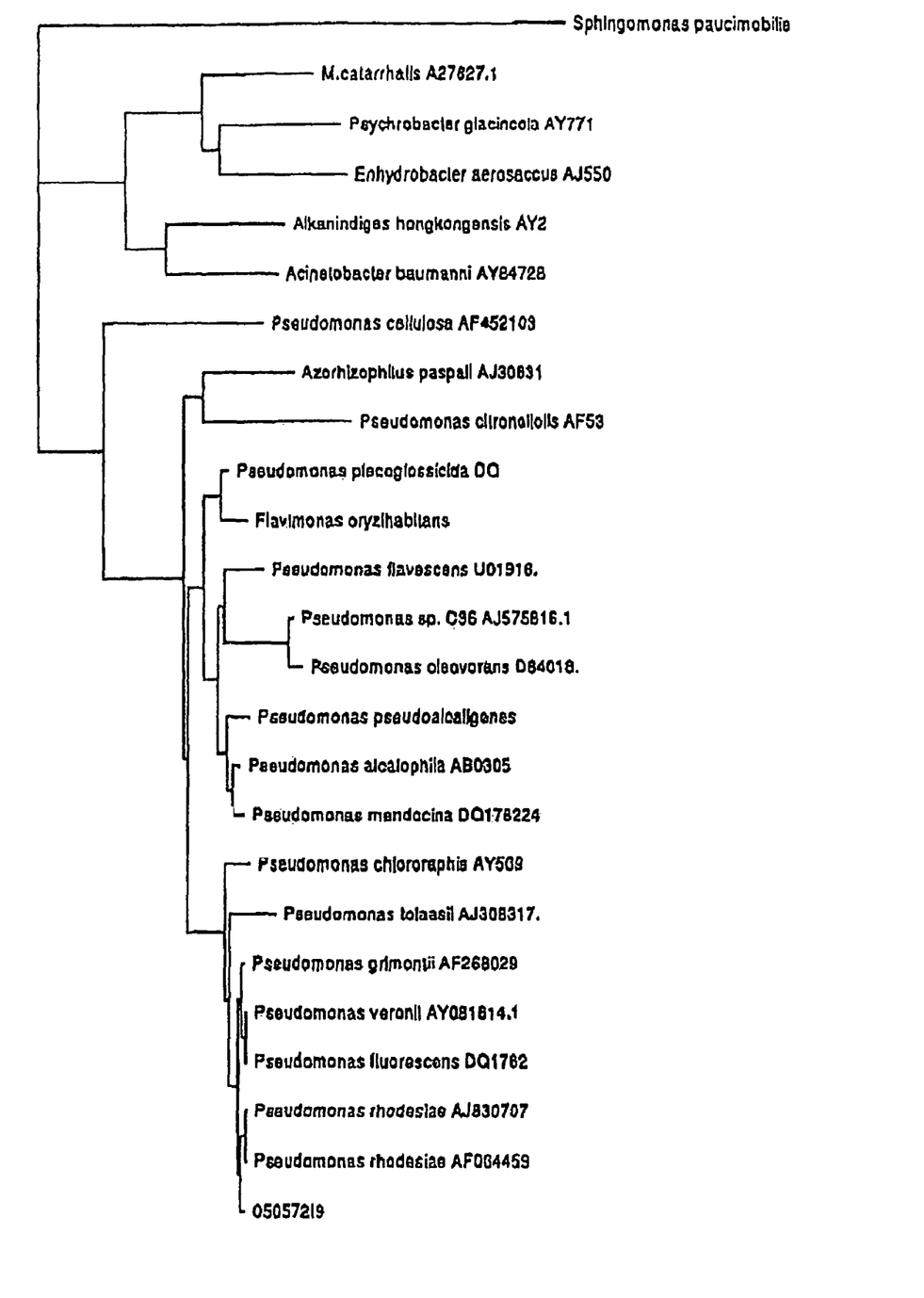
FIG. 1 shows a dendrogram of *Pseudomonas rhodesiae* 05057219 strain (Pseudomonas rhodesiae, FERM BP-10912) of the present invention, which was prepared based on the nucleotide sequence of the 16SrDNA gene.

BLAST homology search was conducted based on the nucleotide sequence of 16SrDNA gene of 05057219 strain. In addition, the nucleotide sequence of 16SrDNA gene of 05057219 strain was analyzed with ClustalW, and the analysis results thus obtained were processed by using Tree View to make a dendrogram of 05057219 strain (FIG. 1). The dendrogram demonstrated the taxonomic position of 05057219 strain. Consequently, it was strongly suggested that 05057219 strain is likely to be *Pseudomonas rhodesiae*.

3. Analysis of Bacterial Properties

Results of the sequence analysis for the 16SrDNA gene in the above "2." suggested that 05057219 strain is highly likely to be a microorganism belonging to *Pseudomonas* genus, especially to be *Pseudomonas rhodesiae* or *Pseudomonas fluorescens*. In order to determine the species of 05057219 strain, its mycological properties were examined by the given method as described later. Bacterial properties of 05057219 strain are as follows. It is a Gram-negative, rod-shaped bacterium, which does not form spore. Its full cell length is 2.0-2.5 μm, the full width is 0.7-0.8 μm, and motility is observed. It forms a smooth circular colony on a broth agar medium and produces fluorescent pigment on a King B medium. Its growth is not observed at 41° C. It is positive for catalase activity, oxidized in the OF test, negative for nitrate salt reduction, negative for indole production, negative for urease activity, positive for gelatin degradation, negative for β-galactosidase activity, and negative for β-glucosidase activity. Further, in LOPAT test, it is positive for levan production, negative for potato tuber rot, negative for tobacco hypersensitive response, positive for oxidase activity, and positive for arginine degradation. It is negative for starch assimilation. As to assimilation of carbon compounds such as sugar and organic acids, it is positive for D-glucose, positive for L-arabinose, positive for D-mannose, positive for D-mannitol, positive for N-acetyl-D-glucosamine, negative for maltose, positive for potassium gluconate, positive for n-capric acid, negative for adipic acid, positive for dL-malic acid, positive for sodium citrate, negative for phenyl acetate, positive for sucrose, positive for trehalose, negative for adonit, positive for sorbitol, positive for butyric acid, positive for propionic acid, and positive for propylene glycol. These results are summarized in a table as below.

TABLE 2

| | 050572I9 strain FERM BP-10912 | Pseudomonas rhodesiae (JCM11940 strain) | Pseudomonas fluorescens (NRRC14160 strain) |
|---|---|---|---|
| Cell form | Rod-shaped | Rod-shaped | Rod-shaped |
| Colony form | Smooth circular | Smooth circular | Smooth circular |
| Gram staining | − | − | − |
| Spore formation | − | − | − |
| Motility | + | + | + |
| Growth at 41° C. | − | | |
| Catalase activity | + | | |
| OF test | Oxidation | Oxidation | Oxidation |
| King B medium test | + | | |
| Reduction of nitrate salt | − | + | − |
| Indole production | − | − | − |
| Urease activity | − | − | − |
| Gelatin degradation | + | + | − |
| β-galactosidase activity | − | − | − |
| β-glucosidase activity | − | − | − |
| Levan activity | + | + | + |
| Potato tuber rot | − | | |
| Tobacco hypersensitive response | − | | |
| Oxidase activity | + | + | + |
| Arginine degradation | + | + | − |
| (Assimilation) | | | |
| Starch | − | − | − |
| D-glucose | + | + | + |
| L-arabinose | + | + | + |
| D-mannose | + | + | + |
| D-mannitol | + | | |
| N-acetyl-D-glucosamine | + | + | + |
| Maltose | − | − | − |
| Potassium gluconate | + | + | + |
| n-capric acid | + | + | + |
| Adipic acid | − | − | − |
| dL-malic acid | + | + | + |
| Sodium citrate | + | + | + |
| Phenyl acetate | − | − | − |
| Sucrose | + | + | − |
| Trehalose | + | + | + |
| Adonit | − | − | + |
| Sorbitol | + | + | + |
| Butyric acid | + | + | − |
| Propionic acid | + | + | − |
| Propylene glycol | + | + | − |

Among the items in Table 2 above, API20NE (bioMerieux Japan Ltd.) was used and the test was conducted according to the enclosed protocol for reduction of nitrate salt, indole production, OF test, arginine degradation, urease activity, gelatin degradation, β-galactosidase activity, β-glucosidase activity, assimilation of D-glucose, assimilation of L-arabinose, assimilation of D-mannose, assimilation of D-mannitol, assimilation of N-acetyl-D-glucosamine, assimilation of maltose, assimilation of potassium gluconate, assimilation of n-capric acid, assimilation of adipic acid, assimilation of dL-malic acid, assimilation of sodium citrate, and assimilation of phenyl acetate. Oxidase activity was tested by using Oxidase Reagent (bioMerieux Japan Ltd.) and catalase activity was tested by using ID color Catalase (bioMerieux Japan Ltd.). Further, a King B medium used in the King B medium test was from EIKEN CHEMICAL CO., LTD. Gram staining was carried out by using Color Gram 2 (bioMerieux Japan Ltd.). In the levan production test; the strain was transferred by streak onto the flat plate of Nutrient agar supplemented with 5% sucrose, and cultured for 3 days at 25° C. Those forming a white and viscous colony which was raised in a large domy shape were determined as positive.

The potato tuber rot test was conducted as follows.
Potatoes peeled and sliced in rounds by 7-8 mm thickness were washed with water and soaked in alcohol, which were then quickly subjected to flame sterilization and placed in Petri dishes and kept under an excessive moisture condition. The round-sliced potato sections were coated with a thick bacterial solution and cultured for 2 days at 25° C. Those potato sections wherein most of the sections inoculated with bacteria had been rotten were determined as positive, and those potato sections wherein only a small part of the inoculated area had been rotten were determined as negative. This test was conducted by using the "Tokachi-kogane" variety as test potatoes.

A hypersensitive response test for tobacco was conducted as follows.

A bacterial solution was injected into mesophyll of tobacco (White Burley or Bright Yellow) with a syringe. Two kinds of bacterial solutions were used, i.e., bacterial solutions with the bacteria concentration of $1 \times 10^8$ cells/ml and $1 \times 10^9$ cells/ml, respectively. Tobaccos injected with respective bacterial solution were cultivated for 5 days. Those tobaccos wherein the part infiltrated with the bacterial solution had suffered from dehydration and turned into brown or dark green were determined as positive. Those tobaccos that showed no change or that simply turned yellowish were determined as negative.

The starch assimilation test was conducted as follows. First, a strain was transferred by streak onto Nutrient agar (containing 35 g agar and 10 g soluble starch in 1 L water), and cultured for 2 to 3 days at 30° C. After the culture, Lugol's iodine solution (containing 0.1 g iodine and 0.2 g potassium iodide in 30 ml water) was poured onto the above-mentioned agar medium, and it was determined positive when a transparent part was observed around the bacterial colony.

Assimilation of carbon compounds such as sugars and organic acids were tested as follows. 5 ml of a basal medium whose composition is as described below was added with 0.1 wt % or 0.2 wt % of a carbon compound (any one of D-glucose, sucrose, trehalose, adonit, sorbitol, butyric acid, propionic acid and propylene glycol; 0.2 wt % for D-glucose, sucrose, trehalose, adonit and sorbitol, and 0.1 wt % for butyric acid, propionic acid and propylene glycol), to prepare the medium. The bacterial cell was inoculated onto thus prepared medium and cultured for 2 to 3 days (5 days for butyric acid) at 30° C. After the culture, it was determined as positive when the bacterial growth was observed.

| Composition of the basal medium (1 L) | |
|---|---|
| 1M $Na_2HPO_4$ and 1M $KH_2PO_4$ buffer (pH 6.8) | 40 mL |
| $(NH_4)_2SO_4$ | 1.0 g |
| Hutner inorganic salt solution | 20 mL |
| Distilled water | Remainder |

| Composition of Hunter inorganic salt solution (1 L) | |
|---|---|
| Nitrilotriacetic acid | 10 g |
| $MgSO_4 \cdot 7H_2O$ | 14.45 g |
| $CaCl_2 \cdot 2H_2O$ | 3.335 g |
| $(NH_4)_6Mo_7O_{24} \cdot 4H_2O$ | 9.25 mg |
| $FeSO_4 \cdot 7H_2O$ | 99 mg |
| Stock solution of salts (Metals "44") | 50 ml |

Nitrilotriacetic acid was dissolved in distilled water and neutralized with potassium hydroxide, then other salts were added thereto.

| Stock solution of salts (composition for 100 ml) | |
| --- | --- |
| EDTA | 250 mg |
| $ZnSO_4 \cdot 7H_2O$ | 1.095 mg |
| $FeSO_4 \cdot 7H_2O$ | 500 mg |
| $MnSO_4 \cdot H_2O$ | 154 mg |
| $CuSO_4 \cdot 5H_2O$ | 39.2 mg |
| $Co(NO_3)_2 \cdot 6H_2O$ | 24.8 mg |
| $Na_2B_4O_7 \cdot 10H_2O$ | 17.7 mg |

In order to demonstrate whether 05057219 strain is *Pseudomonas rhodesiae* or *Pseudomonas fluorescens*, known strains, *Pseudomonas rhodesiae* JCM11940 strain and *Pseudomonas fluorescens* NBRC14160 strain were tested for the items in the above Table 2 in a similar manner to the above. The results are shown in Table 2.

*Pseudomonas fluorescens* is known to be pathogenic to tomatoes and cause tomato pith necrosis. Thus, in order to examine whether 05057219 strain has such pathogenicity to tomatoes or not, the following test was conducted.

05057219 strain was cultured in a liquid medium until $A_{600}$ (absorbance at wave length 600 nm) reaches 1.0, and the culture solution was inoculated by spraying onto the main culm and leafstalk part centering on the leafstalk base of tomato seedlings. After having been cultivated for 7 days, the seedlings were observed and there was no trace of symptom of tomato pith necrosis. The seedlings were also observed after having been respectively cultivated for 14 days and 21 days, and there was no trace of symptom of tomato pith necrosis as well. In addition, the above-mentioned culture solution of 05057219 strain was inoculated to tomato seedlings at the part that had been scratched and a similar test was conducted, but any symptom of tomato pith necrosis was not observed either. Further, the above-mentioned culture solution of 05057219 strain was inoculated by injection into the tomato seedlings using a syringe and a similar test was carried out. Likewise, symptom of tomato pith necrosis was not observed.

The results of Table 2 revealed that 05057219 strain differed from *Pseudomonas fluorescens* NBRC14160 strain in respect of presence or absence of gelatin degradation, arginine acid degradation, sucrose assimilation, adonit assimilation, propionic acid assimilation, and propylene glycol assimilation. On the other hand, 05057219 strain differed from *Pseudomonas rhodesiae* JCM11940 strain only in respect of presence or absence of reduction ability for nitrate salt.

In addition, the bacterial cell forms were observed and it was revealed that 05057219 strain (full cell length; 2.0-2.5 μm, cell width; 0.7-0.8 μm) and *Pseudomonas rhodesiae* JCM11940 strain (full cell length; 2.0-2.5 μm, cell width; 0.7-0.8 μm) were almost the same size, but that *Pseudomonas fluorescens* NBRC14160 strain (full cell length; 2.2-2.7 μm, cell width; 0.8-1.0 μm) were slightly larger than 05057219 strain in both length and width.

Moreover, unlike *Pseudomonas fluorescens*, 05057219 strain did not cause tomato pith necrosis.

From a comprehensive review of the above results, 05057219 strain was thought to be much more homologous to *Pseudomonas rhodesiae* than to *Pseudomonas fluorescens*. Therefore, 05057219 strain was identified as *Pseudomonas rhodesiae*. The present inventors named the 05057219 strain as *Pseudomonas rhodesiae* 05057219 strain. *Pseudomonas rhodesiae* is a microorganism of Bio Safety Level 1.

Analysis results for 05057219 strain using API20NE were searched on the database of National Institute for Agro-Environmental Sciences. Because the search result indicated the possibility of 05057219 strain to be *Pseudomonas marginalis* pv. *marginalis* even at a considerably low probability of 9%, the following test was conducted to verify this possibility by examining whether 05057219 strain is pathogenic or not to Chinese cabbage and lettuce to which *Pseudomonas marginalis* pv. *marginalis* are known to be pathogenic.

A culture solution obtained by subjecting 05057219 strain to a liquid culture was centrifuged and the bacterial cell was recovered. The collected bacterial cell was suspended in water, and water was further added thereto in order to adjust $A_{600}$ of the bacterial cell suspension to be 1.0. The midrib sections of Chinese cabbage were immersed in the bacterial cell suspension. The sections were taken out from the bacterial cell suspension and incubated for 4 days at 28° C. The sections of Chinese cabbage were then observed, but there was no trace of symptom (occurrence of submerged green-brown spots) of Chinese cabbage bacterial rot which is a disease whose pathogenic bacterium is *Pseudomonas marginalis* pv. *marginalis*.

A similar test was conducted by using lettuce instead of Chinese cabbage, but likewise there was no trace of symptom (occurrence of submerged lesion as well as browning and expansion of leaf vein) of lettuce bacterial rot which is a disease whose pathogenic bacterium is *Pseudomonas marginalis* pv. *marginalis*. Further, as shown in Table 2 above, 05057219 strain did not cause tuber rot in potatoes. It was confirmed from these facts that 05057219 strain is not *Pseudomonas marginalis* pv. *marginalis*.

4. Preparation of Bacterial Cell Suspension

To a 300 ml-volume conical flask, 150 ml of a Standard method broth (0.25% yeast extract, 0.5% peptone, 0.1% glucose, pH 7.0) was put in and sterilized by heat. Thereto, 0.1 ml of the preculture of *Pseudomonas rhodesiae* 05057219 strain (FERM BP-10912) was inoculated and cultured for 3 days at 100 rpm at 30° C. in a reciprocating shaker. Thus obtained culture solution was centrifuged to remove the supernatant. The precipitate was washed with water, for which centrifugation was conducted again, then the supernatant was removed and the precipitate was washed with water. The bacterial cell suspension of *Pseudomonas rhodesiae* 05057219 strain was thus prepared.

5. Preparation of a Plant Disease Controlling Wettable Powder Composition

The bacterial cell suspension prepared in "4." above was freeze-dried. The viable bacteria count of the dried material was $1.0 \times 10^{11}$ cfu/g. 10 weight parts of the dried bacterial cell, 9 weight parts of the condensate of (sodium) naphthalene-sulfonate formaldehyde, and 81 weight parts of calcium sulfate and a hydrate thereof were uniformly mixed to obtain a wettable powder composition. The wettable powder composition is a pharmaceutical agent having *Pseudomonas rhodesiae* 05057219 strain as an active ingredient.

TEST EXAMPLE 1

Test for Assessing Controlling Effect Against Bacterial Soft Rot of Lettuce (Indoor Test)

The bacterial cell suspension obtained in the above-mentioned "4." was diluted with water to prepare a treatment solution ($A_{600}$=0.1). The treatment solution was sprayed on the cut end of a leaf cut from the midrib of lettuce. As a comparative example, a 1000-fold dilution of Biokeeper (trademark) wettable powder (CENTRAL GLASS Co., Ltd.) was sprayed in a similar manner. Each lettuce which was subjected to the spray treatment was incubated for 5 hours at 28° C. under a humidified condition. A water suspension ($A_{600}$=0.5) of pathogenic bacterium of bacterial soft rot of lettuce (*Erwinia carotovora*) was inoculated to the cut end of each lettuce, followed by incubation for 4 days at 28° C. Subsequently, the degree of disease onset was investigated according to the following standards, and the disease severity and preventive value were calculated based on formulae 1 and 2 below.

Standard 0: No pathology observed
Standard 1: Pathology is observed in less than 10% of the midrib
Standard 2: Pathology is observed in 10-50% of the midrib
Standard 3: Pathology is observed in 50-75% of the midrib
Standard 4: Pathology exceeds 75% of the midrib $$\text{Disease severity} = \frac{(1 \times n1 + 2 \times n2 + 3 \times n3 + 4 \times n4)}{4 \times (\text{Total number of searched leaves})} \times 100 \quad \text{[Formula 1]}$$

n1 to n4 represent number of leaves respectively corresponding to standards 1 to 4.

Preventive value=(1−(Disease severity in treated area/ Disease severity in untreated area))×100 [Formula 2]

Results of the test for assessing controlling effect against bacterial soft rot of lettuce (indoor test) are shown in Table 3.

TABLE 3

|  | Disease severity survey for bacterial soft rot | |
|---|---|---|
|  | Disease severity | Preventive value |
| *Pseudomonas rhodesiae* 05057219 strain | 20.0 | 72.4 |
| Biokeeper wettable powder | 25.0 | 65.5 |
| Untreated | 72.5 | — |

As is apparent from Table 3, *Pseudomonas rhodesiae* 05057219 strain was confirmed to demonstrate a preventive value of 72.4 and to have a superior controlling effect against bacterial soft rot of lettuce. Moreover, *Pseudomonas rhodesiae* 05057219 strain showed a higher preventive value than that of Biokeeper (trademark) wettable powder which uses non-pathogenic *Erwinia carotovora*.

TEST EXAMPLE 2

Test for Assessing Controlling Effect Against Bacterial Soft Rot in Chinese Cabbage (Field Test)

The bacterial cell suspension obtained in the above-mentioned "4." was diluted with water to prepare a treatment solution ($A_{600}$=0.1). The treatment solution was sprayed on Chinese cabbage planted fixedly in the field. As a comparative example, a 1000-fold dilution of Biokeeper (trademark) wettable powder (CENTRAL GLASS Co., Ltd.) or a 1000-fold dilution of Coppersin (trademark) wettable powder (Meiji Seika Kaisha, Ltd.) was sprayed in a similar manner. The spray treatment was conducted twice with the interval of 1 week. On the day of the first spray treatment, a water suspension ($A_{600}$=0.1) of pathogenic bacterium of bacterial soft rot in Chinese cabbage (*Erwinia carotovora*) was inoculated by spraying. 1 week after the second spray treatment, the degree of disease onset was investigated according to the following standards, and the disease severity, strain onset rate and preventive value were calculated based on formulae 3, 4 and 5 below.

Standard 0: No disease onset
Standard 1: Disease onset is observed in part of outer leaf
Standard 2: Disease onset is observed in part of outer leaf and head leaf
Standard 3: Disease onset is observed in most part of head leaf $$\text{Disease severity} = \frac{(1 \times n1 + 2 \times n2 + 3 \times n3)}{3 \times (\text{Total number of searched strains})} \times 100 \quad \text{[Formula 3]}$$

n1 to n3 represent number of strains respectively corresponding to standards 1 to 3.

$$\text{Strain onset rate} = \frac{(\text{Number of diseased strains}/\text{Total number of searched strains}) \times 100}{} \quad \text{[Formula 4]}$$

$$\text{Preventive value} = 1 - \frac{\text{Disease severity (or strain onset rate) in treated area}}{\text{Disease severity (or strain onset rate) in untreated area}} \times 100 \quad \text{[Formula 5]}$$

Results of the test for assessing controlling effect against bacterial soft rot in Chinese cabbage (field test) are shown in Table 4.

TABLE 4

|  | Disease severity survey for bacterial soft rot | | | |
|---|---|---|---|---|
|  | Disease severity | Preventive value | Strain onset rate | Control level |
| *Pseudomonas rhodesiae* 05057219 strain | 3.7 | 72.2 | 11.1 | 72.3 |
| Biokeeper wettable powder | 10.0 | 25.0 | 30.0 | 25.0 |
| Coppersin wettable powder | 3.3 | 75.0 | 10.0 | 75.0 |
| Untreated | 13.3 | — | 40.0 | — |

As is apparent from Table 4, *Pseudomonas rhodesiae* 05057219 strain has a preventive value of 72.2 relative to the disease severity and a preventive value of 72.3 relative to the strain onset rate, accordingly *Pseudomonas rhodesiae* 05057219 strain was confirmed to have a superior controlling effect against bacterial soft rot in Chinese cabbage. Moreover, the preventive value of *Pseudomonas rhodesiae* 05057219 strain was equal to that of Coppersin (trademark) wettable powder, a chemical controlling agent having basic copper chloride as a major component, and was much higher than that of Biokeeper (trademark) wettable powder using non-pathogenic *Erwinia carotovora*.

TEST EXAMPLE 3

Test for Assessing Controlling Effect Against Citrus Canker (Indoor Test)

The bacterial cell suspension obtained in the above-mentioned "4." was diluted with water to prepare a treatment solution ($A_{600}$=0.1). The treatment solution was sprayed on citrus (lemon) leaves that had been scratched with a surgical knife. As a comparative example, a 1000-fold dilution of Agrept (trademark) wettable powder (Meiji Seika Kaisha, Ltd.) was sprayed in a similar manner, and the leaves were incubated for 5 hours at 28° C. under a humidified condition. A water suspension ($A_{600}$=0.5) of pathogenic bacterium of citrus canker (*Xanthomonas campestris* pv. *citri*) was inoculated at the cut site, followed by incubation for 7 days at 28° C. Subsequently, the degree of disease onset was investigated according to the following standards, and the disease severity and preventive value were calculated based on formulae 6 and 7 below.

Standard 0: No lesion is observed
Standard 1: Lesion is scarcely observed
Standard 2: Lesion is observed
Standard 3: Lesion is remarkably observed $$\text{Disease severity} = \frac{(1 \times n1 + 2 \times n2 + 3 \times n3)}{3 \times (\text{Total searched number})} \times 100 \quad \text{[Formula 6]}$$

n1 to n3 represent number of lesions respectively corresponding to standards 1 to 3.

Preventive value=(1−(Disease severity in treated area/ Disease severity in untreated area))×100   [Formula 7]

Results of the test for assessing controlling effect against citrus canker (indoor test) are shown in Table 5.

TABLE 5

| | Disease severity survey for citrus canker | |
|---|---|---|
| | Disease severity | Preventive value |
| *Pseudomonas rhodesiae* 050572I9 strain | 16.7 | 81.8 |
| Agrept wettable powder | 54.2 | 40.9 |
| Untreated | 91.7 | — |

As is apparent from Table 5, *Pseudomonas rhodesiae* 0505712I9 strain was confirmed to demonstrate a preventive value of 81.8 and to have a superior controlling effect against citrus canker. Moreover, *Pseudomonas rhodesiae* 0505712I9 strain showed a remarkably higher preventive value than that of Agrept (trademark) wettable powder which is a chemical controlling agent comprising streptomycin sulfate as a major component.

TEST EXAMPLE 4

Test for Assessing Controlling Effect Against Citrus Canker (Field Test)

The bacterial cell suspension obtained in the above-mentioned "4." was diluted with water to prepare a treatment solution ($A_{600}$=0.05). The treatment solution was sprayed on all over a navel tree. As a comparative example, a 1000-fold dilution of Coppersin (trademark) wettable powder (Meiji Seika Kaisha, Ltd.) was sprayed in a similar manner. The spray treatment was further conducted 10 days after the flowers were shed, and once after 2 to 3 weeks therefrom, i.e., 3 spray treatments in total. 7 days after the final spray treatment, the degree of disease onset of leaves and fruits of the naval was investigated according to the following standards, and the disease severity, leaf onset rate, young fruit onset rate and preventive value were calculated based on formulae 8, 9, 10 and 11 below.

Standard 0: No lesion is observed
Standard 1: Number of lesions is 1 to 3
Standard 2: Number of lesions is 4 to 10
Standard 3: Number of lesions is 11 to 20
Standard 4: Number of lesions is 21 or more $$\text{Disease severity} = \frac{(1 \times n1 + 2 \times n2 + 3 \times n3 + 4 \times n4)}{(4 \times \text{Total number of searched leaves and young fruits})} \times 100 \quad \text{[Formula 8]}$$

n1 to n4 represent number of leaves and young fruits respectively corresponding to standards 1 to 4.

$$\text{Onset leaf rate} = \text{(Number of diseased leaves/Total number of searched leaves)} \times 100 \quad \text{[Formula 9]}$$

$$\text{Onset young fruit rate} = \text{(Number of diseased young fruits/Total number of searched young fruits)} \times 100 \quad \text{[Formula 10]}$$

$$\text{Preventive value} = 1 - \frac{\text{Disease severity (or strain onset rate) in treated areas}}{\text{Disease severity (or strain onset rate) in untreated area}} \times 100 \quad \text{[Formula 11]}$$

Preventive values relative to the leaf onset rate and the young fruit onset rate were calculated in a similar manner.

Results of the test for assessing controlling effect against citrus canker (field test) are shown in Table 6 (citrus leaf) and Table 7 (citrus young fruit).

TABLE 6

| | Citrus leaf | | | |
|---|---|---|---|---|
| | Disease severity | Preventive value | Leaf onset rate | Preventive value |
| *Pseudomonas rhodesiae* 0505712I9 strain | 4.1 | 72.5 | 12.5 | 67.5 |
| Untreated | 15.0 | — | 38.6 | — |

TABLE 7

| | Citrus young fruit | | | |
|---|---|---|---|---|
| | Disease severity | Preventive value | young fruit onset rate | Preventive value |
| Pseudomonas rhodesiae 050572I9 strain | 13.3 | 77.5 | 32.1 | 60.7 |
| Untreated | 59.2 | — | 81.8 | — |

As is apparent from Tables 6 and 7, *Pseudomonas rhodesiae* 050572I9 strain was confirmed to demonstrate a high preventive value, wherein the preventive value relative to the disease severity in leaves was 72.5 and the preventive value relative to the leaf onset rate was 67.5. In addition, *Pseudomonas rhodesiae* 050572I9 strain was confirmed to demonstrate a high preventive value, wherein the preventive value relative to the disease severity in young fruits was 77.5 and the preventive value relative to the young fruit onset rate was 60.7.

TEST EXAMPLE 5

Test for Assessing Controlling Effect Against Bacterial Soft Rot of Lettuce (Indoor Test)

The bacterial cell suspension obtained in the above-mentioned "4." was diluted with water to prepare a treatment solution ($A_{600}$=0.05). Further, a bacterial cell suspension was prepared by culturing *Pseudomonas rhodesiae* JCM11940 in a similar manner to the above-mentioned "4.". From this bacterial cell suspension, a wettable powder was formulated and prepared in a similar manner to the above-mentioned "5." This wettable powder was diluted with water to prepare a treatment solution ($A_{600}$=0.05). Still further, a bacterial cell suspension was prepared by culturing *Pseudomonas fluorescens* NBRC14160 in a similar manner to the above-mentioned "4.", which bacterial cell suspension was then diluted with water to prepare a treatment solution ($A_{600}$=0.05).

The treatment solution in which the bacterial cell suspension obtained in "4." had been diluted was sprayed on the cut end of a leaf cut from the midrib of lettuce. Further, the treatment solution in which a bacterial cell suspension containing *Pseudomonas rhodesiae* JCM11940 had been diluted was sprayed in a similar manner on the cut end of a leaf cut from the midrib of lettuce. Still further, as a comparative example, the treatment solution in which a bacterial cell suspension containing *Pseudomonas fluorescens* NBRC14160 had been diluted was sprayed in a similar manner on the cut end of a leaf cut from the midrib of lettuce.

Each of the spray-treated lettuce was incubated for 5 hours at 25° C. under a humidified condition. Then a water suspension ($A_{600}$=0.5) of pathogenic bacterium of bacterial soft rot of lettuce (*Erwinia carotovora*) was inoculated at the cut site, followed by incubation for 5 days at 25° C. Subsequently, the degree of disease onset was investigated according to the following standards, and the disease severity and preventive value were calculated based on formulae 12 and 13 below.

Standard 0: No pathology observed
Standard 1: Pathology is observed in less than 10% of the midrib
Standard 2: Pathology is observed in 10-50% of the midrib
Standard 3: Pathology is observed in 50-75% of the midrib
Standard 4: Pathology exceeds 75% of the midrib $$\text{Disease severity} = \frac{(1 \times n1 + 2 \times n2 + 3 \times n3 + 4 \times n4)}{4 \times (\text{Total number of searched leaves})} \times 100 \quad \text{[Formula 12]}$$

n1 to n4 represent number of leaves respectively corresponding to standards 1 to 4.

Preventive value=(1−(Disease severity in treated area/Disease severity in untreated area))×100 [Formula 13]

Results of the test for assessing controlling effect against bacterial soft rot of lettuce (indoor test) are shown in Table 8.

TABLE 8

| | Disease severity survey for bacterial soft rot | |
|---|---|---|
| | Disease severity | Preventive value |
| *Pseudomonas rhodesiae* 050572I9 strain | 15.0 | 82.9 |
| *Pseudomonas rhodesiae* JCM11940 strain | 37.5 | 57.1 |
| *Pseudomonas fruorescence*, NBRC14160 strain | 95.0 | 0.0 |
| Untreated | 87.5 | — |

As is apparent from Table 8, *Pseudomonas rhodesiae* JCM11940 strain was confirmed to demonstrate a preventive value of 57.1 and to have a controlling effect against bacterial soft rot of lettuce, though the effect is inferior to that of *Pseudomonas rhodesiae* 050572I9 strain. On the contrary, *Pseudomonas fruorescence*, which is a related species of *Pseudomonas rhodesiae*, demonstrated a preventive value of 0.0 and was confirmed to have no controlling effect against bacterial soft rot of lettuce.

TEST EXAMPLE 6

Test for Assessing Controlling Effect Against Bacterial Rot of Lettuce (Indoor Test)

The bacterial cell suspension obtained in the above-mentioned "4." was diluted with water to prepare a treatment solution ($A_{600}$=0.05). In this treatment solution, a cut leaf centering on the midrib of lettuce was immersed for 10 min. As a comparative example, a similar immersing treatment was conducted by using a 1000-fold dilution of Vegikeeper (trademark) wettable powder (CENTRAL GLASS Co., Ltd.). Each chemically treated lettuce leaf was incubated for 5 hours at 25° C. under a humidified condition. An aqueous suspension ($A_{600}$=0.01) of the pathogenic bacterium of bacterial rot of lettuce (Pseudomonas cichorii PCL2001) was inoculated to both sides of the cross section of the leaf section by 20 μL each, followed by incubation for 5 days at 25° C. Subsequently, the disease severity was investigated according to the following standards.

Standard 0: No pathology observed
Standard 1: Symptom is observed in less than 10% of the midrib
Standard 2: Symptom is observed in 10-50% of the midrib
Standard 3: Symptom is observed in 50-75% of the midrib
Standard 4: Symptom exceeds 75% of the midrib Disease severity $= \dfrac{(1 \times n1 + 2 \times n2 + 3 \times n3 + 4 \times n4)}{4 \times (\text{Total number of searched leaves })} \times 100$ [Formula 14]

n1 to n4 represent number of leaves respectively corresponding to standards 1 to 4.

Preventive value=(1−(Disease severity in treated area/
Disease severity in untreated area))×100 [Formula 15]

TABLE 9

|  | Disease severity survey for bacterial soft rot | |
| --- | --- | --- |
|  | Disease severity | Preventive value |
| *Pseudomonas rhodesiae* 05057219 strain | 2.5 | 87.5 |
| Vegikeeper wettable powder | 5.0 | 75.0 |
| Untreated | 20.0 | — |

As is apparent from Table 9, *Pseudomonas rhodesiae* 05057219 strain was acknowledged to demonstrate a preventive value of 87.5 and to have a high controlling effect against bacterial rot of lettuce. In addition, *Pseudomonas rhodesiae* 05057219 strain demonstrated a higher preventive value than that of Vegikeeper (trademark) wettable powder.

TEST EXAMPLE 7

Test for Assessing Controlling Effect Against Black Rot in Cabbage (Indoor Test)

The bacterial cell suspension obtained in the above-mentioned "4." was diluted with water to prepare a treatment solution ($A_{600}$=0.05). In this treatment solution, a leaf section cut from the cabbage leaf centering on the leaf vein was immersed for 10 min. As a comparative example, a similar immersing treatment was conducted by using a 1000-fold dilution of Vegikeeper (trademark) wettable powder (CENTRAL GLASS Co., Ltd.). Each chemically treated cabbage leaf was incubated for 5 hours at 25° C. under a humidified condition. An aqueous suspension ($A_{600}$=1.0) of the pathogenic bacterium of black rot in cabbage (*Xanthomonas campestris* pv. *campestris* CAX303) was inoculated to both sides of the cross section of the leaf section by 20 μl each, followed by incubation for 8 days at 25° C. Subsequently, the degree of disease severity was investigated according to the following standards.

Standard 0: No pathology observed

Standard 1: Symptom only emerges at a part of the cut end

Standard 2: Symptom emerges as far as a part of the leaf vein

Standard 3: Symptom emerges all over the leaf vein

Standard 4: Symptom emerges all over the leaf vein and as far as the leaf surface Disease severity $= \dfrac{(1 \times n1 + 2 \times n2 + 3 \times n3 + 4 \times n4)}{4 \times (\text{Total number of searched leaves })} \times 100$ [Formula 16]

n1 to n4 represent number of leaves respectively corresponding to standards 1 to 4.

Preventive value=(1−(Disease severity in treated area/
Disease severity in untreated area))×100 [Formula 17]

TABLE 10

| Wettable powder under test | Disease severity survey for bacterial soft rot | |
| --- | --- | --- |
|  | Disease severity | Preventive value |
| *Pseudomonas rhodesiae* 05057219 strain | 25.0 | 60.0 |
| Vegikeeper wettable powder | 45.0 | 28.0 |
| Untreated | 62.5 | — |

As is apparent from Table 10, *Pseudomonas rhodesiae* 05057219 strain demonstrated a preventive value of 60.0 and to have a high controlling effect against black rot in cabbage. In addition, *Pseudomonas rhodesiae* 05057219 strain demonstrated a higher preventive value than that of Vegikeeper (trademark) wettable powder.

TEST EXAMPLE 8

Test for Assessing Controlling Effect Against Bacterial Shot Hole of Peach (Field Test)

The bacterial cell suspension obtained in the above-mentioned "4." was diluted with water to prepare a treatment solution ($A_{600}$=0.1). The treatment solution was sprayed on all over a peach tree. The first spray treatment was conducted just after the flowers were shed, the spray treatments were subsequently conducted on 7 days, 22 days, 34 days and 49 days after the first treatment, which results in 5 spray treatments in total. 15 days after the second spray treatment, 6 days after the fourth spray treatment, and 8 days after the last spray treatment, new shoots around GL-1 m of the tree were investigated for the numbers of healthy leaves and diseased leaves, and the preventive value was calculated.

TABLE 11

|  | First survey | | Second survey | | Third survey | |
| --- | --- | --- | --- | --- | --- | --- |
|  | Leaf onset rate (%) | Preventive value | Leaf onset rate (%) | Preventive value | Leaf onset rate (%) | Preventive value |
| *Pseudomonas rhodesiae* 05057219 strain | 13.3 | 64.9 | 27.4 | 55.3 | 15.3 | 50.4 |
| Untreated | 38.0 | — | 61.2 | — | 30.8 | — |

As is apparent from Table 11, *Pseudomonas rhodesiae* strain demonstrated a preventive value of about 50-65 and to have a high controlling effect for peaches in the growing season against peach bacterial shot hole.

The invention claimed is:

1. A biologically pure culture of *Pseudomonas rhodesiae* 05057219 strain deposited at the International Patent Organism Depositary (IPOD), National Institute of Advanced Industrial Science and Technology (AIST), under international accession number FERM BP-10912.

2. A plant disease controlling agent comprising an effective amount of a biologically pure culture of a strain of *Pseudomonas rhodesiae* having controlling ability against a plant disease, wherein the strain of *Pseudomonas rhodesiae* is *Pseudomonas rhodesiae* 05057219 strain deposited at the International Patent Organism Depositary (IPOD), National Institute of Advanced Industrial Science and Technology (AIST), under international accession number FERM BP-10912.

3. The plant disease controlling agent according to claim 2, wherein the plant disease is one or more plant diseases selected from the group consisting of canker, bacterial shot hole, bacterial soft rot, bacterial spot, bacterial black spot, bacterial wilt, necrotic leaf spot, pitch necrosis, bacterial grain rot, bacterial seedling blight, bacterial leaf blight, bacterial rot, and black rot.

4. The plant disease controlling agent according to claim 2, wherein the plant disease is a disease in a plant caused by one or more pathogenic bacteria selected from the group consisting of *Xanthomonas* genus, *Erwinia* genus, *Pseudomonas* genus, *Ralstonia* genus, and *Burkholderia* genus.

* * * * *